(12) United States Patent
Scheiwe

(10) Patent No.: US 6,306,896 B1
(45) Date of Patent: Oct. 23, 2001

(54) PHARMACEUTICALLY ACTIVE COMPOSITION CONTAINING ARTEMISININE AND/OR DERIVATIVE OF ARTEMISININE

(75) Inventor: Max Werner Scheiwe, Maulburg (DE)

(73) Assignee: Mepha AG, Aesch (CH)

( * ) Notice: Subject to any disclaimer, the term of this patent is extended or adjusted under 35 U.S.C. 154(b) by 0 days.

(21) Appl. No.: 09/530,637

(22) PCT Filed: Aug. 28, 1998

(86) PCT No.: PCT/CH98/00372

§ 371 Date: Jun. 12, 2000

§ 102(e) Date: Jun. 12, 2000

(87) PCT Pub. No.: WO99/22727

PCT Pub. Date: May 14, 1999

(30) Foreign Application Priority Data

Nov. 3, 1997 (CH) .................................................... 2535/97

(51) Int. Cl.⁷ .................................................. A61K 31/335
(52) U.S. Cl. ............................................. 514/450; 514/895

(58) Field of Search ...................................... 514/450, 895

(56) References Cited

U.S. PATENT DOCUMENTS

| 4,920,147 | 4/1990 | McChesney et al. | 514/450 |
| 5,023,353 | 6/1991 | McChesney et al. | 549/348 |
| 5,639,761 | * 6/1997 | Francois et al. | 514/307 |
| 5,827,681 | * 10/1998 | Krug et al. | 435/34 |

* cited by examiner

*Primary Examiner*—Kevin E. Weddington
(74) *Attorney, Agent, or Firm*—Hoffmann & Baron, LLP

(57) ABSTRACT

The invention relates to a pharmaceutically active composition containing a substance which is active against malaria parasites and shows a high level of activity against multi-resistant lines of *Plasmodium falciparum*. The inventive composition is characterized in that it contains the active agent artemisinine and/or a derivative of artemisinine in a carrier material which is inert with the active agent, in a pharmaceutically active quantity and in that the carrier material is essentially free of compounds with a hydrophilic-lipophilic balance between 7 and 9.9.

19 Claims, No Drawings

PHARMACEUTICALLY ACTIVE COMPOSITION CONTAINING ARTEMISININE AND/OR DERIVATIVE OF ARTEMISININE

The present invention relates to a pharmaceutically active composition which contains a substance active against malaria parasites and has a high activity against multiresistant lines of *Plasmodium falciparum*. The present invention relates in particular to an acceptable form of artemisinin and/or a derivative of artemisinin, for example arteether, artemether, artemisin or artesunate, especially artesunate, for rectal administration. Artesunate is a water-soluble derivative of artemisinin. Artemisinin (qinghaosu) is obtained from the leaves of the shrub *Artemisia annua* and is a naturally occurring sesquiterpene lactone with an endo peroxide group. Because of the low water solubility of the natural substance artemisinin, attempts have been made to convert it to a variety of synthetic derivatives in order to improve the pharmaceutical availability. One such derivative is artesunate. Artemisinin and artesunate are efficient active substances in the treatment of malaria. Artemisinin preparations are currently the substances which act most rapidly against malaria parasites. In particular, they show a high activity against multiresistant lines of *Plasmodium falciparum*. Also, when administered to humans, only a few side effects and no significant toxicity have been observed, although neurotoxicity has occurred in animals. Nevertheless, relatively little has hitherto been disclosed about the pharmacogenetics of artemisinin and artesunate, which may be connected with the complicated analytical methods needed to quantify these drugs in the blood.

In the body, both artemisinin and artesunate are converted to dihydroartemisinin (DHA, artesol), which is the actual schizonticidal active substance. Artemisinin and artesunate can therefore be regarded as prodrugs for dihydroartemisinin.

Artesunate corresponds to the compound dihydroartemisinin hemisuccinate and its salts, especially its sodium salt. Dihydroartemisinin has the chemical name $3\alpha,12\alpha$-epoxy-3,4,5,5a$\alpha$,6,7,8a$\alpha$,9,10,12$\beta$,12a-dodecahydro-10-hydroxy-3$\beta$,6$\alpha$,9$\beta$-trimethylpyrano[4,3-j]-1,2-benzodioxepine. Dihydroartemisinin is also known by the name dihydroqinghaosu. Artesunate, or dihydroartemisinin hemisuccinate, can be prepared for example by converting dihydroartemisinin to dihydroartemisinin hemisuccinate by means of acylation. Arteether, artemether and artemisin are known per se.

Artemisinin, artesunate, dihydroartemisinin and derivatives thereof are manufactured especially in China and Vietnam and are marketed for example in tablet form. In severe cases of malaria (possibly cerebral) caused by *Plasmodium falciparum*, the patients are often unconscious and an oral treatment is not possible. The parenteral administration of quinine, for example, is only permitted in hospitals. In such cases artesunate in a rectal form of administration can save lives throughout the world and in practically any situation. A further advantage of the rectal form is administration to children, where oral use is often complicated by swallowing problems. Rectal forms of artesunate can also be administered successfully for other types of malaria, e.g. VIVAX.

Approximately one million children die of malaria every year in Africa. Although tablets and injectable solutions (as a powder preparation) are already commercially available, suppositories are not. This is principally connected with the fact that artesunate is unstable in conventional suppository formulations, especially at elevated temperature. Numerous areas, for example subtropical and tropical regions, often have an exceptionally warm climate and hence also above-average temperatures. Furthermore, by their very nature, suppositories are generally unstable at elevated outside temperatures since they are intended to melt at approx. 37° C.

The object of the present invention is to find a rectal pharmaceutical form containing artemisinin and/or a derivative of artemisinin, for example arteether, artemether, artemisin and/or artesunate, especially artesunate, as the active substance, this form having an adequate stability of the active substance for the appropriate storage period and containing a sufficient amount of active substance to allow reliable control of the Plasmodium pathogens in the blood. Examples of rectal forms are suppositories, rectal foams, enemas or rectal capsules. The term artesunate will be used predominantly hereafter to represent artemisinin and its derivatives.

The conventional prerequisite for the production of rectal capsules is the presence in every case of surface-active substances, especially wetting agents (surfactants), but also emulsifiers and optionally washing-active substances, in order to assure an adequate bioavailability of the active substance by improving the distribution in the rectum. However, studies have shown that such artesunate formulations have a high degree of instability even after a short storage period.

Surface-active substances are subdivided according to their hydrophilic-lipophilic balance, i.e. by means of their HLB values, into antifoams (HLB values of 1–3), emulsifiers (HLB values of 4–6 and 8–18), wetting agents (HLB values of 7–9), washing-active substances (HLB values of 13–15) and solubilizers (HLB values of 10–18). The boundaries between these effects overlap partially and are fluid. Depending on the composition in which it is present, a compound may exhibit its assigned effect inadequately, if at all, despite its HLB value, or it may act for example both as an emulsifier and as a wetting agent. Compounds referred to as antifoams, emulsifiers, wetting agents, washing-active substances and solubilizers are known per se.

It has now been found, surprisingly, that a composition which is substantially free of compounds with an HLB value in the range 7–9.9, and which contains the active substance artemisinin and/or a derivative of artemisinin, especially artesunate, in an excipient which is inert towards the active substance, not only gives a medicinally stable formulation which satisfies the requisite criteria in respect of the chemical stability of the active substance, but also has an active substance bioavailability which is within the internationally recognized limits applied to comparative bioavailability.

In terms of the present invention, the expression "substantially free of compounds with an HLB value in the range 7–9.9" means that any compound present with an HLB value in the range 7–9.9, preferably a compound with an HLB value in the range 7–9, has a concentration in the composition of at most 10 percent by weight, preferably at most 5 percent by weight and particularly preferably at most 2 percent by weight, based on the weight of the pharmaceutically active substance. It is usually preferred that no compound with an HLB value in the range 7–9.9, preferably no compound with an HLB value in the range 7–9, be present in the composition.

The present invention is defined in the claims. In particular, the invention relates to a pharmaceutically active composition which contains a substance active against malaria parasites and has a high activity against multiresistant lines of *Plasmodium falciparum*, characterized in that this composition contains a pharmaceutically effective amount of the active substance artemisinin and/or a derivative of artemisinin in an excipient which is inert towards the active substance, and the excipient is substantially free of compounds with an HLB value in the range 7–9.9, preferably in the range 7–9.

The expression "artemisinin and derivatives of artemisinin" is to be understood as meaning especially arteether, artemether, artemisin and/or artesunate, preferably artesunate.

The present invention further relates to the use of the composition according to the invention for the production of pharmaceutical forms for rectal administration. Such forms for rectal administration are preferably suppositories, rectal foams, enemas and rectal capsules.

The present invention further relates to rectal forms, preferably suppositories, rectal foams, enemas or rectal capsules, particularly preferably suppositories and rectal capsules, which contain a composition according to the invention. Rectal capsules are preferred.

The present invention further relates to suppositories, characterized in that they consist of a hard gelatin capsule or a soft gelatin capsule containing a pharmaceutically effective amount of the composition according to the invention, the hard gelatin capsule or the soft gelatin capsule being provided with a lubricating coating consisting of coating materials known per se for rectal capsules. Suppositories consisting of a soft gelatin capsule are preferred. The present invention further relates to the use of these suppositories for controlling malaria parasites and multiresistant lines of *Plasmodium falciparum*.

The composition according to the invention is preferably also substantially free of compounds with an HLB value in the ranges 4–6.9 and 10–13. In other words, any such compound present in the composition has a concentration of at most 10 percent by weight, preferably at most 5 percent by weight and particularly preferably at most 2 percent by weight, based on the weight of the pharmaceutically active substance. It is usually preferred that no compound with an HLB value in the ranges 4–6 and 10–13, preferably in the ranges 4–6.9 and 10–13, be present in the composition.

The composition according to the invention is preferably also substantially free of compounds with an HLB value in the range 13.1–15. In other words, any such compound present in the composition has a concentration of at most 10 percent by weight, preferably at most 5 percent by weight and particularly preferably at most 2 percent by weight, based on the weight of the pharmaceutically active substance. It is usually preferred that no compound with an HLB value in the range 13–15, preferably in the range 13.1–15, be present in the composition.

Suppositories and rectal capsules are preferred. Suppositories are intended to melt at about 37° C. In hot countries where the average temperature is already 37° C. or above, rectal capsules are therefore used, while in latitudes where the average temperatures are below 37° C., it is preferred to use suppositories.

Artesunate is dihydroartemisinin hemisuccinate ($C_{19}H_{28}O_8$) and has the formula

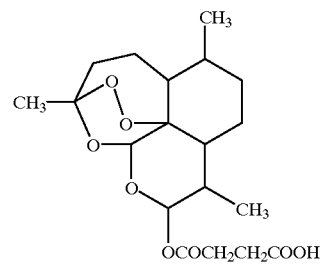

(I)

Wetting agents can be anionic, cationic, amphoteric or non-ionic. Conventional wetting agents have an HLB value of about 7–9 and are e.g. anionic wetting agents such as alkali metal or ammonium salts of unsaturated fatty acids, especially alkali metal alkylsulfates, e.g. sodium dodecylsulfate, sodium laurylsulfate, sodium cetylstearylsulfate or sodium docosanoate, alkali metal and alkaline earth metal salts of alkyl- or arylalkylsulfonates, salts of gallic-acid, such as sodium cholate, and acidic saponins. Examples of cationic wetting agents are quaternary ammonium compounds. Examples of amphoteric wetting agents are lecithins and betaine derivatives. Examples of non-ionic wetting agents are fatty alcohols, cholesterols, optionally in combination with primary emulsifiers, e.g. emulsifying cetylstearyl alcohol (a combination of sodium cetylstearylsulfate and cetylstearyl alcohol) or cetomacrogol emulsifying wax, cholesterol, partial fatty acid esters of glycerol, such as glycerol fatty acid monoesters, e.g. glycerol monostearate, optionally in combination with hydrophilic emulsifiers, partial fatty acid esters of sorbitan, ethoxylated partial fatty acid esters of sorbitan, other partial fatty acid esters, fatty acid esters of polyoxyethylene, fatty alcohol ethers of polyoxyethylene, fatty acid esters of sucrose, fatty acid esters of polyglycerol, and block copolymers of polyoxyethylene and polyoxypropylene. Such surfactants are normally used in an amount of 1 to 10 percent, based on the filling weight. According to the present invention, it is preferred not to use wetting agents.

Excipients which are inert towards the active substance are especially waxes, fats and oils, as well as mixtures thereof. These can be of vegetable or animal origin and can also be hydrogenated. Waxes, fats and oils of vegetable origin are preferred. It is also possible to use paraffin waxes and paraffin oils.

Examples of waxes are natural plant waxes, such as carnauba wax, waxes of animal origin, such as yellow or white beeswax, and stearin waxes with melting points (or melting point ranges) of between about 47° C. and about 88° C. However, it is also possible to use paraffin waxes, for example hard paraffins with melting points of between about 47° C. and about 65° C., and microcrystalline waxes with melting points of between about 54° C. and about 105° C. Such waxes are used principally as bodying agents.

Fats are generally triglycerides of $C_{18}$–$C_{24}$ fatty acids and predominantly $C_{18}$–$C_{19}$ fatty acids with melting points or melting point ranges of between about 28° C. and about 45° C. Hard fats in the form of semisynthetic fats for the production of suppositories consist of a mixture of mono-, di- and triglycerides of saturated $C_{10}$–$C_{18}$ fatty acids. It is also possible to use paraffin fats, i.e. paraffins with melting points or melting point ranges in the ranges-mentioned. Fats are the actual excipient.

Oils are generally medium-chain triglycerides of $C_8$–$C_{16}$ fatty acids and pre-dominantly $C_8$–$C_{12}$ fatty acids which are liquid at room temperature and have melting points or melting point ranges of between 0° C. and 20° C. and preferably of about 0° C. to 10° C. It is also possible to use paraffin oils, i.e. paraffins with melting points or melting point ranges in the ranges mentioned. Oils are used principally as solvents or solubilizers, as suspension aids or as emulsifiers.

Such fats and/or oils can be obtained for example from plant raw materials such as coconuts, palm kernels, olives or rape-seed, or from animal raw materials such as tallow, lard or blubber, and may be hydrogenated.

The weight ratio of the pharmaceutical active substance to the excipient is preferably 5% to 15%, particularly preferably 7% to 12% and very particularly preferably about 8.5% to 9.5%, based on the total weight of the excipient. The pharmaceutically active dose for adults is generally in the range from 150 mg to 250 mg per capsule and averages about 200 mg, corresponding to an average dose of about 3 mg/kg body weight.

The consistency of the preparation according to the invention is not critical as it has practically no influence on the stability of the active substance. The preparation can have a solid, pasty or liquid consistency. The decisive factor governing the choice of the weight ratio of the active substance to the excipient and the selection of the various components of the excipient is the industrial processability of the preparation in the capsule filling process. Also, the suspension must not throw a deposit during filling, i.e. it is necessary to assure the uniformity of content of the preparation in the capsule during and after filling. For this purpose the flowability of the preparation, which is normally in the form of a suspension, is adjusted so that the preparation flows well during processing but takes the form of a paste or solidifies after processing, in the filled state in the capsule. This is achieved by processing the preparation under pressure and/or a slightly elevated temperature in the filling process. It is also possible to incorporate additives into the preparation to facilitate said processing, examples being finely divided (disperse/highly disperse) aluminium oxide or disperse/highly disperse silicon oxide. Such a consistency is easy to produce and presents no problems for those skilled in the art.

The quality and nature of the capsules used correspond to the commercially available qualities known per se. The production of the soft gelatin capsules preferred according to the invention is described e.g. in Pharmazeutische Technologie (Pharmaceutical Technology), H. Sucker, P. Fuchs, P. Speiser, Stuttgart 1991, pages 337–347.

The purpose of the capsule coating is to improve the lubrication of the rectal form and ensure that it is easy to insert into the body. Such lubricating coatings are known per se. Examples of coating materials known per se for rectal capsules are polyethylene glycols with average molecular weights of about 1550 and 20,000, glycerol monooleate and glycerol dioleate, polyvinyl acetate and talcum. Thus a composition known per se consists for example of 40.5 parts of polyethylene glycol with an average molecular weight of about 20,000, 17.4 parts of polyethylene glycol with an average molecular weight of about 1550, 26.0 parts of glycerol monooleate and glycerol dioleate (mixture), 1.2 parts of polyvinyl acetate and 14.9 parts of talcum. Capsule coatings are described for example in Pharmazeutische Technologie (Pharmaceutical Technology), H. Sucker, P. Fuchs, P. Speiser, Stuttgart 1991, page 343.

The preparation according to the invention can be manufactured for example by mixing the excipients, e.g. the hard fat, at the melting point in a suspension processing unit capable of being heated and evacuated. Other excipients, for example medium-chain triglycerides, and the active substance are then added to the melt, after which the melt is processed to a homogeneous mass. The molten suspension obtained is then filtered through a sieve, after which the filtrate is degassed by the application of a vacuum and filled into capsules. The capsules obtained in this way are provided with a coating in a manner known per se. It is also possible to choose a different procedure, which creates no problems per se for those skilled in the art.

The Examples below illustrate the invention.

EXAMPLE 1

Preparation of a Composition According to the Invention 30.6 kg of hard fat are melted at 45° C. in a stainless steel suspension processing unit capable of being heated and evacuated, which has a built-in stirrer, homogenizer and forced circulation system (Diessel-Werke). 44.4 kg of medium-chain triglycerides are then incorporated, with stirring, followed by 7.5 kg of artesunate. The mass is then homogenized for 10 minutes under forced circulation. The suspension is then kept at 40° C.±2° C., with moderate stirring, and passed through a sieve of mesh size 400 µm. The filtered suspension is degassed for 2 to 3 hours by the application of a vacuum (residual pressure 0.5 to 0.2 bar absolute). The mixture obtained is filled into soft gelatin capsules as described in Example 10. The batch is sufficient for 150,000 capsules containing 50 mg.

EXAMPLES 2–8

The Examples listed in Table 1 were prepared analogously to Example 1.

TABLE 1

| Example no. | Artesunate mg | Hard fat mg | Medium-chain triglyceride mg | Additives |
| --- | --- | --- | --- | --- |
| 2 | 200 | 40 | 350 | — |
| 3 | 200 | 20 | 570 | — |
| 4 | 50 | 32 | 359 | — |
| 5 | 50 | 4 | 387 | — |
| 6 | 400 | 15 | 175 | — |
| 7 | 200 | 21 | 369 | groundnut oil, 35 mg stearic acid, 10 mg Aerosil, 3 mg |
| 8 | 200 | 21 | 369 | — |

EXAMPLE 9

Comparative Example 25.2 kg of hard fat are melted at 45° C. in a stainless steel suspension processing unit capable of being heated and evacuated, which has a built-in stirrer, homogenizer and forced circulation system (Diessel-Werke). 37.8 kg of medium-chain triglycerides, 0.75 kg of soya lecithin and 12.75 kg of polyoxyethylene glycol triricinoleate are then added, the mixture is homogenized and 7.5 kg of artesunate are added. The mass is then homogenized for 10 minutes under force circulation. The suspension is kept at 40° C.±2° C., with moderate stirring, and then passed through a sieve (mesh size 400 µm). The filtered suspension is degassed for 2 to 3 hours by the application of a vacuum (residual pressure 0.5 to 0.2 bar absolute). The mixture obtained is filled into soft gelatin capsules as described in Example 10. The batch is sufficient for 150,000 capsules containing 50 mg.

EXAMPLE 10

Production of Soft Gelatin Capsules (a) 46 kg of gelatin, 19.8 kg of glycerol (85%) and 34.2 kg of purified water are introduced into a separated, heatable stainless steel tank equipped with a stirrer (Diessel). The mass is melted at 70° C. to give a clear melt. Gas bubbles are removed by stirring slowly. A suspension of 1.26 kg of titanium dioxide in glycerol (85%) (1 part of titanium dioxide to 1 part of 85% glycerol) and 0.14 kg of yellow iron oxide in 85% glycerol (1:2), in 0.7 kg of purified water, is added to the melt and the mixture is stirred until the distribution is homogeneous. This mixture is used for several batches of capsules.

(b) The mass prepared as described in section (a) is introduced into an encapsulating machine, with cooling, and used encapsulate a composition according to Examples 1–8 by the rotary die process of R. P. Scherer. The capsules are predried in a rotary dryer (Scherer system) until they are sufficiently firm. The capsules are then dried further on trays, the incoming air being at a temperature of 15 to 26° C. at a relative humidity of 10–40%. When drying is complete, defective capsules are discarded.

(c) A perforated coating drum (Glatt GC) is used to provide the capsules with the lubricating coating. The lacquer formulation is sprayed on under forced air circulation until the requisite amount per capsule has been applied. Each batch of coating material is obtained by dissolving or suspending 0.6675 kg of polyethylene glycol with an average molecular weight of 20,000, 0.2865 kg of polyethylene glycol with an average molecular weight of 1550, 0.429 kg of glycerol monooleate and dioleate (mixture), 0.0195 kg of polyvinyl acetate and 0.2475 kg of talcum in an ethanol/water mixture. The coated capsules are dried and inspected, defective capsules being discarded. The capsules are then sealed into PVDC/aluminium blister packs.

Stability Testing of the Preparations

The compositions prepared as described in Examples 1–8 and Comparative Example 9 above, filled into rectal capsules (produced as described in Example 10), were subjected to a stability test under the following storage conditions:

1. conditions at room temperature: 20–25° C., relative humidity: 60%, storage period: 6 to 24 months
2. in the drying cabinet:
   (i) 31° C., relative humidity: 75%, storage period: 6–24 months
   (ii) 40° C., relative humidity: 75%, storage period: 6–24 months
   (iii) 41° C., relative humidity: 75%, storage period: 6–24 months After storage, the following aspects were examined: the appearance of the preparation (discoloration etc.), the average weight (nominal value: 894 mg±10%), the filling weight, the disintegration time in water at 37° C., and the content of artesunate and, as degradation products, dihydroartemisinin (artesol) and artemisinin. It was found that a high degree of instability of the comparative preparation of Example 9 occurred after only a short time (i.e. after 3 months at 40° C. and 75% relative humidity and after 6 months at 31° C. and 75% relative humidity), so the experiments were not continued. After 3 months at 40° C. and 75% relative humidity, the content of artesunate dropped to 86.6%. Artesol (6%) and artemisinin (2.2%) were found as by-products. The analysis results obtained after 6 months at 31° C. and 75% relative humidity were analogous.

By contrast, the preparations of Examples 1–8 were found to have an excellent stability. At room temperature (20–25° C.) and a relative humidity of 60%, the content of artesol and artemisinin was unmeasurable after 13 months. The content of artesunate remained unchanged at 102.3%.

After storage for 13 months in a drying cabinet at 31° C. and a relative humidity of 75%, analysis showed the following values: artesol: 0.5%, artemisinin: unmeasurable, artesunate: 100.3%.

After storage for 13 months in a drying cabinet at 40° C. and a relative humidity of 75%, analysis showed the following values: artesol: 2.0%, artemisinin: unmeasurable, artesunate: 89.5%.

These results confirm that the stability of the composition according to the invention is 3 years at room temperature.

What is claimed is:

1. A pharmaceutical composition in the form for rectal administration active against malaria parasites and multiresistant lines of *Plasmodium falciparum*, comprising a pharmaceutically effective amount of an active substance selected from the group consisting of artemisinin, derivatives of artemisinin and combinations thereof, and an excipient which is inert towards the active substance, and which excipient is substantially free of compounds with an HLB value in the range of about 7 to about 9.9.

2. The composition according to claim 1, wherein said artemisinin derivative is selected from the group consisting of artemether, artemisin and/or artesunate, and combinations thereof.

3. The composition according to claim 1, wherein any compound with an HLB value of 7–9.9 is present in the composition in an amount of at most 10 percent by weight of the total composition.

4. The composition according to claim 1, wherein any compound with an HLB value of 7–9.9 is present in the composition in an amount of at most 5 percent by weight of the total composition.

5. The composition according to claim 1, wherein any compound with an HLB value of 7–9.9 is present in the composition in an amount of at most 2 percent by weight of the total composition.

6. The composition according to claim 1, wherein no compound with an HLB value of 7–9.9 is detectable in the composition.

7. The composition according to claim 1, wherein the concentration of compounds with an HLB value in the ranges of 4–6.9 and 10–13 is at most 10 percent by weight, based on the weight of the active substance, and wherein no compound with an HLB value in the ranges of 4–6.9 and 10–13 is detectable in the composition.

8. The composition according to claim 1, wherein the concentration of compounds with an HLB value in the ranges of 4–6.9 and 10–13 is at most 5 percent by weight, based on the weight of the active substance, and wherein no compound with an HLB value in the ranges of 4–6.9 and 10–13 is detectable in the composition.

9. The composition according to claim 1, wherein the concentration of compounds with an HLB value in the ranges of 4–6.9 and 10–13 is at most 2 percent by weight, based on the weight of the active substance, and wherein no compound with an HLB value in the ranges of 4–6.9 and 10–13 is detectable in the composition.

10. The composition according to claim 1, wherein the concentration of compounds with an HLB value in the range of 13.1–15 is at most 10 percent by weight, based on the weight of the active substance, and wherein no compound with an HLB value in the range of 13.1–1 is detectable in the composition.

11. The composition according to claim 1, wherein the concentration of compounds with an HLB value in the range of 13.1–15 is at most 5 percent by weight, based on the weight of the active substance, and wherein no compound with an HLB value in the range of 13.1–1 is detectable in the composition.

12. The composition according to claim 1, wherein the concentration of compounds with an HLB value in the range of 13.1–15 is at most 2 percent by weight, based on the weight of the active substance, and wherein no compound with an HLB value in the range of 13.1–1 is detectable in the composition.

13. The composition according to claim 1, wherein said excipient may be selected from the group consisting of waxes, fats, and oils, and combinations thereof, and wherein said waxes, fats, and oils are of vegetable or animal origin.

14. The composition according to claim 1, wherein said excipient may be selected from the group consisting of paraffin waxes, paraffin oils, and combinations thereof.

15. The composition according to claim 1, wherein the weight ratio of said active substance to said excipient is 5% to 15%.

16. The composition according to claim 1, wherein said composition is in the form of suppositories, rectal foams, enemas, or rectal capsules.

17. The composition according to claim 16, wherein said suppositories comprise a soft gelatin capsule containing a pharmaceutically active substance in a pharmaceutically effective amount.

18. The composition of claim 17, wherein said soft gelatin capsule is provided with a lubricating coating.

19. A method of controlling malaria parasites and multi-resistant lines of *Plasmodium falciparum* by administering rectally to a patient the composition of claim 1.

* * * * *

(12) EX PARTE REEXAMINATION CERTIFICATE (5128th)
United States Patent
Scheiwe

(10) Number: US 6,306,896 C1
(45) Certificate Issued: Jun. 28, 2005

(54) PHARMACEUTICALLY ACTIVE COMPOSITION CONTAINING ARTEMISININE AND/OR DERIVATIVE OF ARTEMISININE

(75) Inventor: Max Werner Scheiwe, Maulburg (DE)

(73) Assignee: Mepha AG, Aesch (CH)

Reexamination Request:
No. 90/006,269, Apr. 24, 2002

Reexamination Certificate for:
Patent No.: 6,306,896
Issued: Oct. 23, 2001
Appl. No.: 09/530,637
Filed: Jun. 12, 2000

(22) PCT Filed: Aug. 28, 1998
(86) PCT No.: PCT/CH98/00372
§ 371 (c)(1),
(2), (4) Date: Jun. 12, 2000
(87) PCT Pub. No.: WO99/22727
PCT Pub. Date: May 14, 1999

(30) Foreign Application Priority Data
Nov. 3, 1997 (CH) .................................... 2535/97

(51) Int. Cl.⁷ .......................................... A61K 31/335
(52) U.S. Cl. ....................................... 514/450; 514/895
(58) Field of Search ............................... 514/450, 895; 424/456

(56) References Cited
FOREIGN PATENT DOCUMENTS
WO          9202217         2/1992

OTHER PUBLICATIONS

H.A.C. Titulaer et al., "The pharmacokinetics of artemisinin . . . ", J. Pharm. Pharmacol, 1990, Feb. 5, 1990, pp. 810–813.
H. Sucker et al., Pharmazeutische Technologie (Pharmaceutical Tech.), Stuttgart 1991, pp. 337–347, Trans. provided.
S. Looareesuwan et al., "Efficacy and tolerability . . . ", Annals of Trop. Med., vol. 89, No. 5, 469–475 (1995).
Ha Vinh et al., "Severe and complicated . . . ", Tran. Royal Soc. of Trop. Med., (1997) 91, 465, 467.
S. Looareesuwan et al., "A comparative clinical . . . ", Am. J. Trop. Med. Hyg., 57(3), 1997, pp. 348–353.
Tran Tinh Hien et al., "Comparison of artemisinin . . . ", Tran. Royal Soc. Trop. Med., (1992) 86, 582–583.
Tran Tinh Hien et al., "Comparative effectiveness of artemisinin . . . ", Tran. Royal Soc. Trop. Med., (1991) 85, 210–211.
Guo–Qiao Li et al., "Clinical trials of artemisinin . . . ", Tran. Royal Soc. Trop. Med., (1994) 88, Supplement 1, 5–6.
Keith Arnold et al., "A randomized comparative study of . . . ", Tran. Royal Soc. Trop. Med., (1990) 84, 499–502.
Li Guoqiao et al., "Observation on the Efficacy of . . . ", J. Trad. Chinese Med., 5(3):159–161, 1985.

*Primary Examiner*—Frederick Krass

(57) ABSTRACT

The invention relates to a pharmaceutically active composition containing a substance which is active against malaria parasites and shows a high level of activity against multi-resistant lines of *Plasmodium falciparum*. The inventive composition is characterized in that it contains the active agent artemisinine and/or a derivative of artemisinine in a carrier material which is inert with the active agent, in a pharmaceutically active quantity and in that the carrier material is essentially free of compounds with a hydrophilic-lipophilic balance between 7 and 9.9.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 3–5 are cancelled.

Claims 1 and 13 are determined to be patentable as amended.

Claims 2, 6–12 and 14–19, dependent on an amended claim, are determined to be patentable.

New claims 20–24 are added and determined to be patentable.

1. A pharmaceutical composition in [the] *a* form for rectal administration active against malaria parasites and multiresistant lines of *Plasmodium falciparum*, comprising a pharmaceutically effective amount of an active substance selected from the group consisting of artemisinin, derivatives of artemisinin and combinations thereof, and an excipient *selected from the group consisting of waxes, fats and oils, and combinations thereof,* which is inert towards the active substance, [and which excipient is substantially free of compounds with an HLB value in the range of about 7 to about 9.9] *wherein said composition is storage stable for 6 months at 40° C. and 75 percent relative humidity; and*

(*i*) *said waxes are selected from natural plant waxes or waxes of animal origin with melting points of between 47° C. and 88° C., paraffin waxes with melting points of between 47° C. and 65° C. and microcrystalline waxes with melting points of between 54° C. and 105° C.;*

(*ii*) *said fats are selected from triglycerides of $C_{18}$–$C_{24}$ fatty acids with melting points or melting point ranges between 28° C. and 45° C., hard fats in the form of semisynthethic fats consisting of a mixture of mono-, di-, and triglycerides of saturated $C_{10}$–$C_{18}$ fatty acids and paraffin fats with melting points between 28° C. and 45° C.;*

(*iii*) *said oils are selected from medium-chain triglycerides of $C_8$–$C_{16}$ fatty acids which have melting points or melting point ranges of between 0° C. and 20° C. and paraffin oils which have melting points or melting point ranges of between 0° C. and 20° C.;*

(*iv*) *and wherein any compound with an HLB of 7–9.9 is present in the composition in an amount of at most 2 percent by weight of the total composition.*

13. The composition according to claim 1, [wherein said excipient may be selected from the group consisting of waxes, fats, and oils, and combinations thereof, and] wherein said waxes, fats, and oils are of vegetable or animal origin.

20. *A pharmaceutical composition according to claim 1, wherein:*

(*i*) *said waxes are selected from hard paraffin waxes with melting points of between 47° C. and 65° C. and microcrystalline waxes with melting points of between 54° C. and 105° C.;*

(*ii*) *said fats are selected from triglycerides of $C_{18}$–$C_{19}$ fatty acids with melting points or melting point ranges of between 28° C. and 45° C., hard fats in the form of semisynthetic fats consisting of a mixture of mono-, di-, and triglycerides of saturated $C_{10}$–$C_{18}$ fatty acids and paraffin fats with melting points between 28° C. and 45° C.; and*

(*iii*) *said oils are selected from medium-chain triglycerides of $C_8$–$C_{12}$ fatty acids, which have melting points or melting point ranges of between 0° C. and 10° C., and paraffin oils which have melting points or melting point ranges of between 0° C. and 10° C.*

21. *A pharmaceutical composition according to claim 1, wherein said excipient is selected from fats, oils, and combinations thereof.*

22. *A pharmaceutical composition according to claim 20, wherein said excipient is selected from fats, oils, and combinations thereof.*

23. *A pharmaceutical composition according to claim 22, wherein:*

(*ii*) *said fats are selected from hard fats in the form of semisynthetic fats consisting of a mixture of mono-, di-, and triglycerides of saturated $C_{10}$–$C_{18}$ fatty acids and paraffin fats with melting points between 28° C. and 45° C.; and*

(*iii*) *said oils are selected from medium-chain triglycerides of $C_8$–$C_{12}$ fatty acids, which have melting points or melting point ranges of between 0° C. and 10° C.*

24. *A pharmaceutical composition according to claim 23, wherein:*

(*ii*) *said fats are selected from hard fats in the form of semisynthetic fats consisting of a mixture of mono-, di-, and triglycerides of saturated $C_{10}$–$C_{18}$ fatty acids; and*

(*iii*) *said oils are selected from medium-chain triglycerides of $C_8$–$C_{12}$ fatty acids, which have melting points or melting point ranges of between 0° C. and 10° C.*

\* \* \* \* \*